United States Patent
Hirose (10) Patent No.: US 10,918,323 B2
(45) Date of Patent: Feb. 16, 2021

(54) DROWSINESS DETECTING DEVICE, DROWSINESS DETECTING METHOD, AND PROGRAM RECORDING MEDIUM

(71) Applicant: Panasonic Intellectual Property Management Co., Ltd., Osaka (JP)

(72) Inventor: Yoshifumi Hirose, Kyoto (JP)

(73) Assignee: PANASONIC INTELLECTUAL PROPERTY MANAGEMENT CO, LTD., Osaka (JP)

( * ) Notice: Subject to any disclaimer, the term of this patent is extended or adjusted under 35 U.S.C. 154(b) by 363 days.

(21) Appl. No.: 16/003,579

(22) Filed: Jun. 8, 2018

(65) Prior Publication Data

US 2019/0008434 A1  Jan. 10, 2019

(30) Foreign Application Priority Data

Jul. 4, 2017  (JP) .............................. JP2017-130908
May 10, 2018  (JP) .............................. JP2018-091182

(51) Int. Cl.
| | | |
|---|---|---|
| A61B 5/04 | (2006.01) | |
| A61B 5/16 | (2006.01) | |
| A61B 5/0456 | (2006.01) | |
| G16H 50/20 | (2018.01) | |
| A61B 5/00 | (2006.01) | |
| A61B 5/024 | (2006.01) | |
| A61B 5/18 | (2006.01) | |

(52) U.S. Cl.
CPC ............ *A61B 5/16* (2013.01); *A61B 5/02405* (2013.01); *A61B 5/0456* (2013.01); *A61B 5/18* (2013.01); *A61B 5/7282* (2013.01); *G16H 50/20* (2018.01); *A61B 2503/22* (2013.01)

(58) Field of Classification Search
CPC ........... A61B 5/16; A61B 5/18; A61B 5/0456; A61B 5/7282; A61B 5/02405; A61B 2503/22; G16H 50/20
See application file for complete search history.

(56) References Cited

U.S. PATENT DOCUMENTS

2018/0365961 A1* 12/2018 Katsuhara .............. G08B 21/06

FOREIGN PATENT DOCUMENTS

WO  2016/104498  6/2016

* cited by examiner

*Primary Examiner* — Mallika D Fairchild
(74) *Attorney, Agent, or Firm* — McDermott Will and Emery LLP (57) ABSTRACT

A drowsiness detecting device includes a feature extractor, a detecting rule storage unit, a normalizer, and a drowsiness detector. The feature extractor extracts a feature value on heartbeats of a user based on intervals between the heartbeats. The detecting rule storage unit retains a detecting rule for drowsiness detecting. The normalizer updates a normalization coefficient. The drowsiness detector detects drowsiness of the user based on the feature value, the detecting rule, and the normalization coefficient. The normalizer updates the normalization coefficient based on the feature value when the drowsiness detector does not detect the drowsiness of the user.

13 Claims, 5 Drawing Sheets

DROWSINESS DETECTING DEVICE, DROWSINESS DETECTING METHOD, AND PROGRAM RECORDING MEDIUM

BACKGROUND

1. Technical Field

The present disclosure relates to a drowsiness detecting device, a drowsiness detecting method, and a program recording medium that detect drowsiness of a user.

2. Description of the Related Art

WO 2016/104498 A1 discloses a drowsiness detecting device.

SUMMARY

The present disclosure provides a drowsiness detecting device that normalizes a value used for drowsiness detecting based on a drowsiness detecting result to accurately detect drowsiness.

The drowsiness detecting device according to the present disclosure includes a feature extractor, a detecting rule storage unit, a normalizer, and a drowsiness detector. The feature extractor is configured to extract a feature value on heartbeats of a user based on intervals between the heartbeats. The detecting rule storage unit is configured to retain a detecting rule for drowsiness detecting. The normalizer is configured to update a normalization coefficient. The drowsiness detector is configured to detect drowsiness of the user based on the feature value, the detecting rule, and the normalization coefficient. The normalizer is configured to update the normalization coefficient based on the feature value when the drowsiness detector does not detect the drowsiness of the user.

It should be noted that these general or specific aspects may be implemented by using a system, a method, an integrated circuit, a computer program, or a computer-readable recording medium such as a compact disc read only memory (CD-ROM), and may also be implemented by any combination of the system, the method, the integrated circuit, the computer program, and the recording medium.

The drowsiness detecting device according to the present disclosure is capable of normalizing a value used for drowsiness detecting based on a drowsiness detecting result to accurately detect drowsiness. Further, even for the same person, the feature value on heartbeats fluctuates with time. The drowsiness detecting device according to the present disclosure is capable of accurately detect drowsiness even for the same person and with a time lapse.

DETAILED DESCRIPTION

Hereinafter, an exemplary embodiment will be described in detail with reference to the drawings as appropriate. However, detailed description beyond necessity may be omitted. For example, detailed description of a matter that has been already known well or overlapping description of substantially the same configuration may be omitted. Such omissions are aimed to prevent the following description from being redundant more than necessary, and to help those skilled in the art easily understand the following description.

It should be noted that the inventor of the present disclosure provides the attached drawings and the following description for those skilled in the art to fully understand the present disclosure, and the attached drawings and the following description are not intended to limit the subject matter as described in the appended claims.

First Exemplary Embodiment

Drowsiness detecting device 10 of a first exemplary embodiment will be described below with reference to FIG. 1 to FIG. 5C.

1. Configuration

Figure 1:
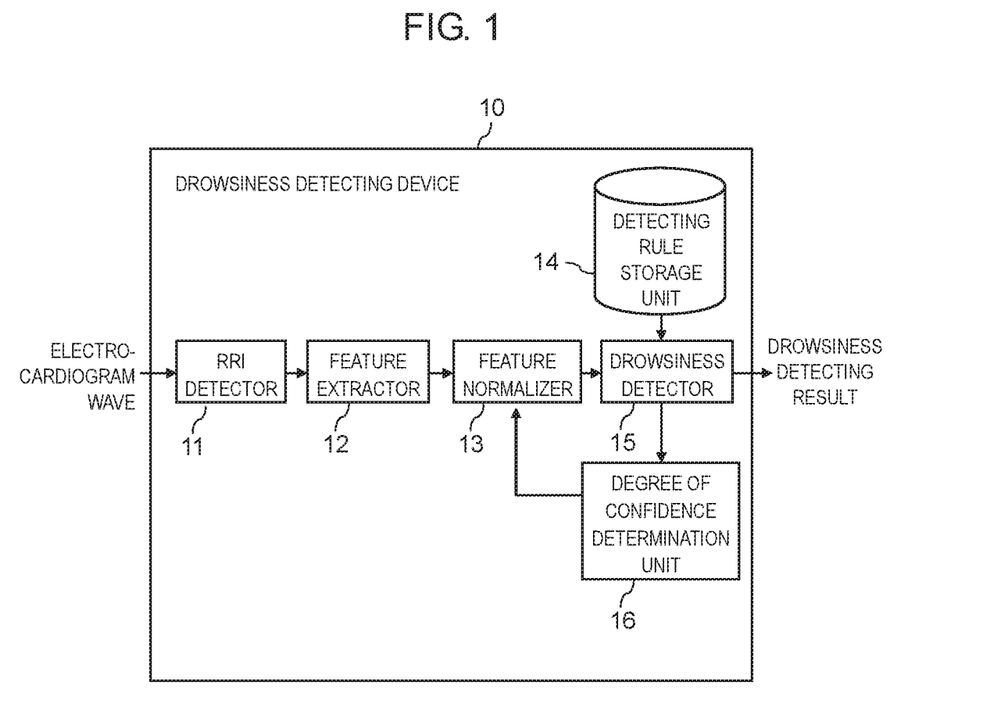
FIG. 1 is a block diagram of a drowsiness detecting device according to a first exemplary embodiment.

FIG. 1 is a block diagram illustrating drowsiness detecting device 10 according to the first exemplary embodiment. Drowsiness detecting device 10 includes RRI detector 11, feature extractor (feature value extractor) 12, feature normalizer (feature value normalizer) 13, detecting rule storage unit 14, drowsiness detector 15, and degree of confidence determination unit 16. Feature normalizer 13 is one example of a normalizer.

RRI detector 11 detects an RRI based on an electrocardiogram wave of (electrocardiogram information on) a user input from the outside. The RRI is a time interval between two adjacent R waves on an electrocardiogram wave. Feature extractor 12 extracts a feature value on heart rate variability (described below) based on the RRI detected by RRI detector 11. Feature normalizer 13 normalizes the feature value extracted by feature extractor 12 based on a normalization coefficient (described below). Detecting rule storage unit 14 retains a detecting rule used for detecting drowsiness from the feature value thus normalized. Drowsiness detector 15 detects presence or absence of drowsiness based on the feature value normalized by feature normalizer 13 and the detecting rule retained by detecting rule storage unit 14. Degree of confidence determination unit 16 determines a degree of confidence of presence or absence of drowsiness detected by drowsiness detector 15.

Drowsiness detecting device 10 includes a processor, a volatile storage region (primary storage device), and a non-volatile storage region (secondary storage device). The volatile storage region is used as a work area used for execution of a control program. The non-volatile storage region stores the control program, content, and the like. The volatile storage region is, for example, a random access memory (RAM). The non-volatile storage region is, for example, a read only memory (ROM), a flash memory, or a hard disk drive (HDD). Functionality of drowsiness detecting device 10 is entirely or partially implemented by, for example, the control program executed by the processor.

Each constituent component will be described in detail below.

1-1. RRI Detector 11

Figure 2:
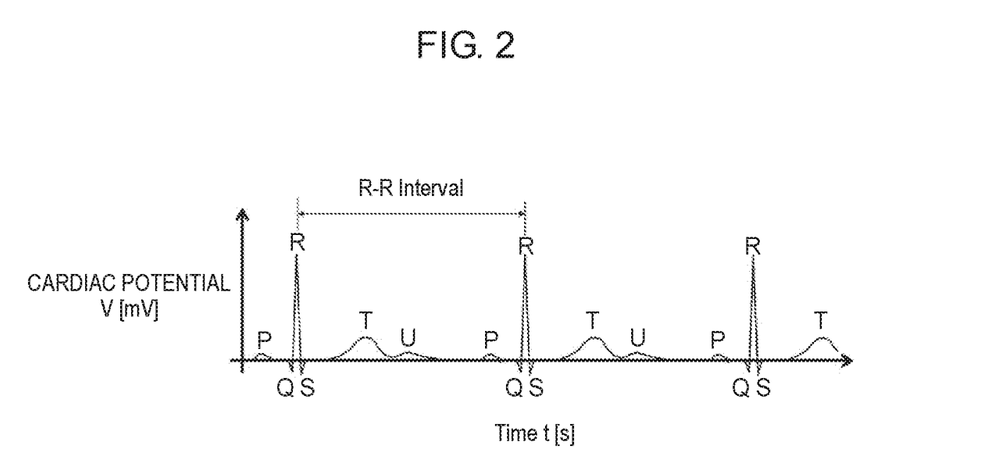
FIG. 2 is a schematic graph showing an example of an electrocardiogram wave input to an R-R interval (RRI) detector.

RRI detector 11 receives the electrocardiogram wave of the user from an external device. Such an electrocardiogram wave generally has a P wave, a Q wave, an R wave, an S wave, a T wave, and a U wave for each heartbeat as shown in FIG. 2. In FIG. 2, a horizontal axis represents time t, and a vertical axis represents cardiac potential V. On the electrocardiogram wave, the R wave has a large amplitude and sharply changes per unit time. Accordingly, the R wave is used for heartbeat detection. A specific method for detecting the R wave is not particularly limited. For example, a time at which a maximum amplitude appears in a section where the amplitude is equal to or greater than a predetermined threshold value may be detected as an R wave time, thus allowing the R wave to be detected. An interval between the R wave time thus detected and an R wave time previously detected is called an RRI. RRI detector 11 detects such an RRI.

1-2. Feature Extractor 12

Feature extractor 12 extracts the feature value for drowsiness detecting based on the RRI input from RRI detector 11. As such a feature value, a feature value on heart rate variability can be used. The feature value on heart rate variability can be calculated from time series of RRIs included in a predetermined time section. A method for setting the time section is not particularly limited. A length of the time section can be set to, for example, 60 seconds. The shorter the length of the time section is, the quicker the time tracking of the heart rate variability is. Conversely, as the length of the time section is short, the RRIs may be responsive to errors in the RRIs caused by, for example, a body motion. Accordingly, it is desirable that the length of the time section is suitably set.

The feature value on heart rate variability can be calculated from time series of the RRIs included in the predetermined time section. Such a feature value on heart rate variability includes a feature value in a time domain and a feature value in a frequency domain.

As the feature value on heart rate variability in the time domain, the following feature values can be used:

Mean RRI: mean RRI in the time section;
Mean heart rate: mean heart rate in the time section;
SDNN: standard deviation of RRIs in the time section;
RMSSD: root mean square of differences between successive adjacent RRIs in the time section;
NN50: number of pairs of successive adjacent RRIs that differ by more than 50 ms in the time section; and
pNN50: proportion of successive adjacent RRIs that differ by more than 50 ms in the time section.

On the other hand, as the feature value on heart rate variability in the frequency domain, the following feature values can be used, provided that spectral analysis is performed on RRIs in the time section:

Low frequency (LF): spectral power in a frequency band from 0.04 Hz to 0.15 Hz;
High frequency (HF): spectral power in a frequency band from 0.15 Hz to 0.4 Hz; and
LF/HF: ratio of spectral power in LF to spectral power in HF.

Figure 3:
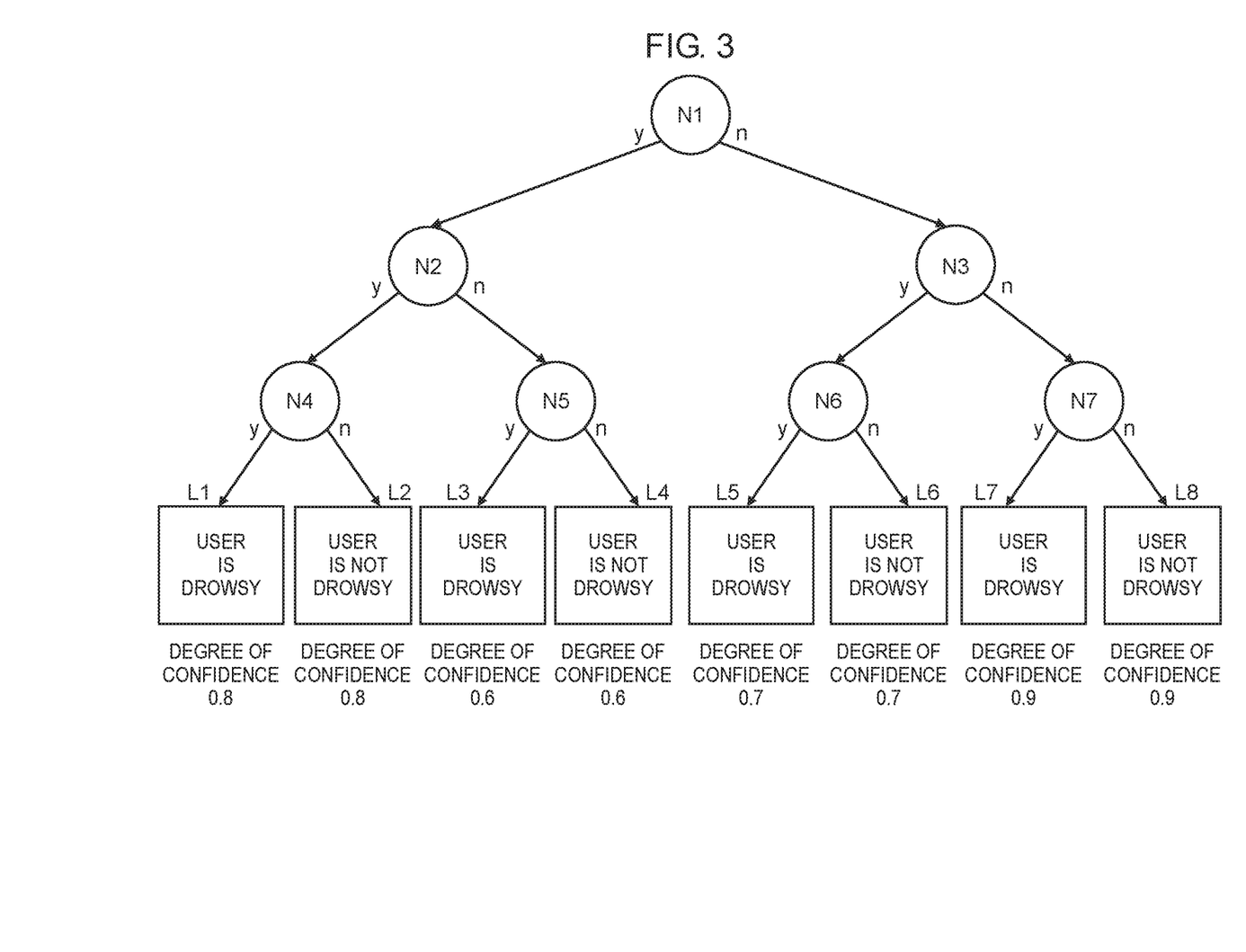
FIG. 3 is a schematic diagram illustrating an example of a detecting rule retained by a detecting rule storage unit.

The feature value extracted by feature extractor 12 is not limited to the above-described feature values. In addition to the above-described feature values, a different feature value acquired from the electrocardiogram wave may be added. Alternatively, the different feature value acquired from the electrocardiogram wave may be replaced with one of the above-described feature values. It should be noted that in a case where drowsiness detecting device 10 uses such a decision tree as is illustrated in FIG. 3, feature extractor 12 may extract a plurality of feature values.

Feature value F extracted as described above is represented by Formula 1.

$$F=[F_1 F_2 \ldots F_N] \qquad \text{[Formula 1]}$$

where $F_k$ represents a feature value in k-th time section. The time sections are represented by respective symbols of 1 to N.

1-3. Feature Normalizer 13

Feature normalizer 13 normalizes feature value $F_k$ in current time section k extracted by feature extractor 12. Here, feature normalizer 13 calculates normalization coefficient $C_k$ based on feature values in time sections from which degree of confidence determination unit 16 (described below) detects that "user is not drowsy" with a degree of confidence greater than predetermined degree of confidence. Then, feature normalizer 13 normalizes feature value $F_k$ with normalization coefficient $C_k$.

Specifically, time sections determined that "user is not drowsy" with a greater degree of confidence in a range from a predetermined time before to a time section immediately before current time section k are represented by respective symbols of p1 to pL. Here, L represents a number of sections determined that "user is not drowsy" with a greater degree of confidence in a range from the predetermined time before to a time section immediately before current time section k. Feature normalizer 13 is capable of calculating the normalization coefficient from Formula 2.

$$C_k = \frac{1}{L}\sum_{l=1}^{L} F_{pl} \qquad \text{[Formula 2]}$$

In other words, feature normalizer 13 calculates, as normalization coefficient $C_k$, a mean of the feature values in the time sections determined that "user is not drowsy" with a greater degree of confidence in a range from the predetermined time before to a time section immediately before current time section k. Feature normalizer 13 calculates, from Formula 3, normalized feature value $FN_k$ with feature value $F_k$ and normalization coefficient $C_k$ thus calculated.

$$FN_k = \frac{F_k}{C_k} \qquad \text{[Formula 3]}$$

It should be noted that a formula used for calculation of normalization coefficient $C_k$ is not limited to Formula 2.

Normalization coefficient $C_k$ may be any normalization coefficient that is determined based on feature values in time sections determined that "user is not drowsy" with a greater degree of confidence. For example, as shown in Formula 4, normalization coefficient $C_K$ may be calculated as a weighted sum of normalization coefficient. $C_{k-1}$ previously calculated and feature value $F_{pL}$ in a last section determined that "user is not drowsy" with a greater degree of confidence.

$$C_k=(1-r)C_{k-1}+rF_{pL} \quad \text{[Formula 4]}$$

where r represents a coefficient used for calculation of the weighted sum. Coefficient r ranges from 0 to 1 and indicates how much priority is given to feature value $F_{pL}$.

A method for setting coefficient r is not particularly limited. Coefficient r may be set to a fixed value such as 0.8. Alternatively, in a case where a degree of confidence determined by degree of confidence determination unit 16 (described below) is great, coefficient r is correspondingly set large. In a case where the degree of confidence is low, coefficient r is correspondingly set small. As described above, coefficient r may be set such that the last feature value with a greater degree of confidence is given higher priority.

It should be noted that, in Formula 3, normalized feature value $FN_k$ is calculated from division of feature value $F_k$ by normalization coefficient $C_k$. However, as shown in Formula 5, normalized feature value $FN_k$ may be calculated from subtraction of normalization coefficient $C_k$ from feature value $F_k$.

$$FN_k=F_k-C_k \quad \text{[Formula 5]}$$

In other words, drowsiness may be detected in accordance with a ratio to the feature value determined that "user is not drowsy", or drowsiness may be detected in accordance with a difference from the feature value determined that "user is not drowsy".

1-4. Detecting Rule Storage Unit 14

Detecting rule storage unit 14 stores the detecting rule used for determination that "user is drowsy" or "user is not drowsy" from normalized feature value $FN_k$ calculated by feature normalizer 13. For example, in a case where drowsiness is determined based on a decision tree, detecting rule storage unit 14 stores a detecting rule in such a decision tree as is illustrated in FIG. 3.

The decision tree illustrated in FIG. 3 is created based on such a learning algorithm as Iterative Dichotomiser 3 (ID3). A plurality of nodes N1 to N7 in the decision tree are associated with the plurality of respective feature values F1 to F7 on heartbeats of the user described above. The decision tree further includes a plurality of threshold values T1 to T7 associated with the plurality of respective nodes N1 to N7. Specifically, node N1 is associated with feature value F1 and threshold value T1, and node N2 is associated with feature value F2 and threshold value T2. The other nodes are also associated with the respective feature values and threshold values.

For example, in a case where feature value F1 is less than threshold value T1 in node N1, transition is made to node N2. In a case where feature value F2 is less than threshold value T2 in node N2, transition is made to node N4. In a case where feature value F4 is less than threshold value T4 in node N4, transition reaches leaf node L1. Then, drowsiness detector 15 determines that "user is drowsy". On the other hand, in a case where feature value F4 is equal to or greater than threshold value T4 in node N4, transition reaches leaf node L2. Then, drowsiness detector 15 determines that "user is not drowsy". As described above, in each of the nodes, a comparison is made between the feature value and the threshold value that are associated with the node. Each of the leaf nodes stores a degree of confidence of "user is not drowsy" or "user is drowsy". For example, leaf node L1 stores 0.8 as the degree of confidence of "user is drowsy", and leaf node L2 stores 0.8 as the degree of confidence of "user is not drowsy". Detecting rule storage unit 14 stores such a detecting rule as is described above. It should be noted that the degree of confidence of "user is not drowsy" and the degree of confidence of "user is drowsy" are determined by degree of confidence determination unit 16 (described below).

Although a rule storing method based on the decision tree is described above, the present disclosure is not limited to the method. For example, the detecting rule may be implemented by a method with a plurality of decision trees, called a random forest. A number of the plurality of decision trees in the random forest is, for example, 100. With the random forest, "user is not drowsy" or "user is drowsy" is determined in each of the decision trees, and a determination having a larger total number becomes a determination result of drowsiness.

1-5. Drowsiness Detector 15

Drowsiness detector 15 determines whether "user is not drowsy" or "user is drowsy" based on feature value $FN_k$ normalized by feature normalizer 13 and the detecting rule stored in detecting rule storage unit 14. Drowsiness detector 15 detects the drowsiness of the user in accordance with the detecting rule stored in detecting rule storage unit 14.

1-6. Degree of Confidence Determination Unit 16

Degree of confidence determination unit 16 determines how much degree of confidence CM with which drowsiness detector 15 detects the drowsiness that is either "user is not drowsy" or "user is drowsy".

An example where the decision tree stored in detecting rule storage unit 14 is used will be described in detail. In a case where the decision tree is created in accordance with, for example, ID3 algorithm, a larger determination result in a leaf node (in this case, "user is not drowsy" or "user is drowsy") becomes a determination result. At this time, degree of confidence CM can be calculated from a ratio between "user is not drowsy" and "user is drowsy" in the leaf node. For example, the ratio between "user is not drowsy" and "user is drowsy" in leaf node L1 of FIG. 3 is 2:8. In this case, degree of confidence CM of "user is drowsy" in leaf node L1 is 0.8. As described above, degree of confidence determination unit 16 can determine the degree of confidence of "user is not drowsy" or the degree of confidence of "user is drowsy" detected by drowsiness detector 15. It should be noted that such a degree of confidence can be determined from a pre-created learned model.

It should be noted that although description has been given above of the example where drowsiness detector 15 detects the drowsiness based on the decision tree, the present disclosure is not limited to the example. For example, in a case where drowsiness detector 15 detects the drowsiness with the random forest, degree of confidence determination unit 16 can calculate degree of confidence CM from the number (W) of decision trees determined that "user is not drowsy" or "user is drowsy" out of the plurality (M) of decision trees determined. In other words, degree of confidence determination unit 16 can calculate degree of confidence CM from the following formula:

$$CM = W/M.$$

2. Operation

Figure 4:
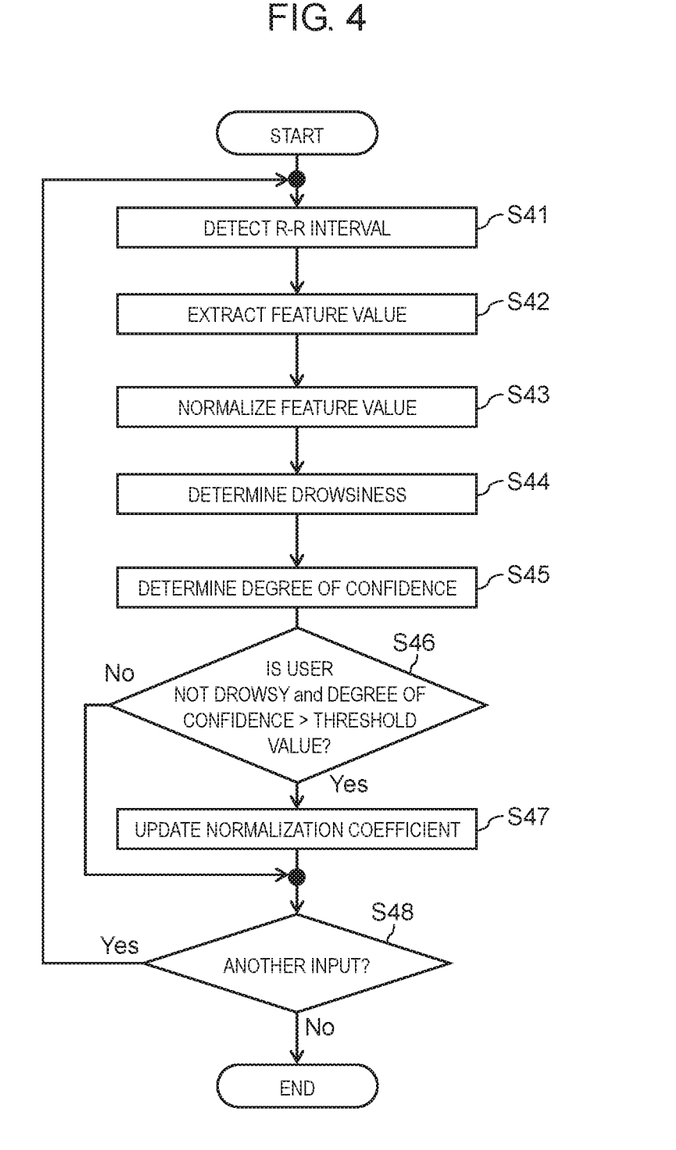
FIG. 4 is a flowchart illustrating an operation of the drowsiness detecting device according to the first exemplary embodiment.

The operation of the first exemplary embodiment will be described in more detail below with reference to a flowchart illustrated in FIG. 4.

RRI detector 11 detects the RRI based on the electrocardiogram wave of the user input from the outside (S41). A specific method for detecting the R wave is not particularly limited. For example, a time at which a maximum amplitude appears in a section where the amplitude is equal to or greater than a predetermined threshold value may be detected as an R wave time, thus allowing the R wave to be detected. An interval between the R wave time thus detected and an R wave time previously detected is called an RRI. RRI detector 11 detects such an RRI.

Feature extractor 12 extracts the feature value for drowsiness detecting based on the RRI input from RRI detector 11 (S42). The feature value to be extracted by feature extractor 12 includes feature values on heart rate variability such as Mean RRI, Mean heart rate, SINN, RMSSD, NN50, pNN50, LF, HF, and LF/HF. The feature value is not limited to the above-described feature values, provided that the feature value is calculated based on heartbeats.

Feature normalizer 13 normalizes feature value $F_k$ extracted by feature extractor 12 (S43). Feature normalizer 13 updates normalization coefficient $C_k$ based on feature values in time sections in which degree of confidence determination unit 16 detects that "user is not drowsy" with a degree of confidence greater than predetermined degree of confidence. Then, feature normalizer 13 normalizes feature value $F_k$ in current time section k based on normalization coefficient $C_k$. It should be noted that degree of confidence determination unit 16 has yet to determine a degree of confidence at the start of the operation; thus, feature normalizer 13 may normalize feature value $F_k$ with normalization coefficient $C_k$ set to 1. Alternatively, an assumption can be established that "user is not drowsy" at the start of the operation; thus, the normalization coefficient at the start may be set to $F_1$ (feature value at the start). Yet alternatively, a predetermined normalization coefficient may be used.

Drowsiness detector 15 determines the drowsiness, that is, either "user is not drowsy" or "user is drowsy", based on feature value $FN_k$ normalized by feature normalizer 13 and the detecting rule stored in detecting rule storage unit 14 (S44). In a case where the determination result indicates that "user is drowsy", the user can be notified of the determination result.

Degree of confidence determination unit 16 determines a degree of confidence with which drowsiness detector 15 determines that "user is not drowsy" or "user is drowsy" (S45).

Feature normalizer 13 checks if degree of confidence CM, with which drowsiness detector 15 detects "user is not drowsy" in step S44 and which is determined in step S45, is greater than the predetermined degree of confidence threshold value (S46).

In a case where step S46 results in Yes ("user is not drowsy" and degree of confidence CM is greater than the predetermined degree of confidence threshold value), feature normalizer 13 updates the normalization coefficient (S47). Then, feature normalizer 13 normalizes the feature value based on the normalization coefficient thus updated.

RRI detector 11 determines whether another electrocardiogram wave is input, and in a case where another electrocardiogram wave is input, the operation returns to step S41. In a case where no electrocardiogram wave is input, the operation is terminated (S48).

In a case where step S46 results in No ("user is drowsy", or degree of confidence CM is equal to or less than the predetermined degree of confidence threshold value), the operation proceeds to step S48.

The above-described operation causes drowsiness detecting device 10 to normalize the feature value for drowsiness detecting based on a drowsiness detecting result. With this configuration, accurate drowsiness detecting less susceptible to differences between individuals is achieved.

Figure 5A:
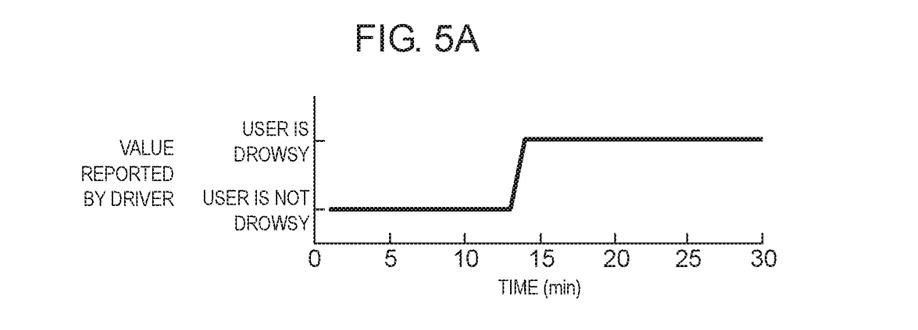
FIG. 5A is a graph showing an example of drowsiness detecting based on a value reported by a driver according to the first exemplary embodiment.
Figure 5B:
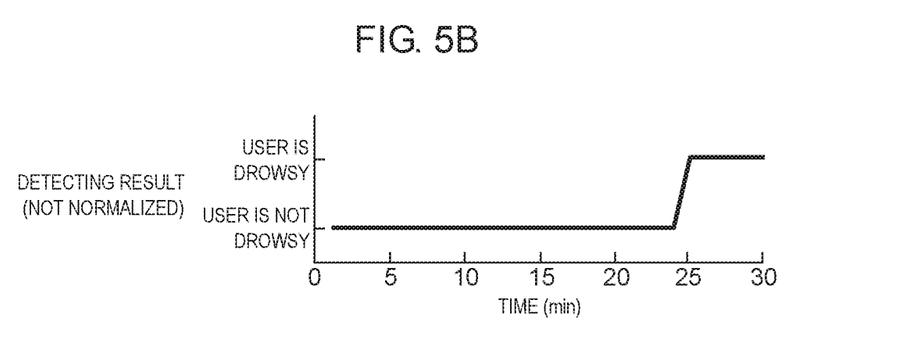
FIG. 5B is a graph showing an example of drowsiness detecting in a case where a feature value is not normalized according to the first exemplary embodiment.
Figure 5C:
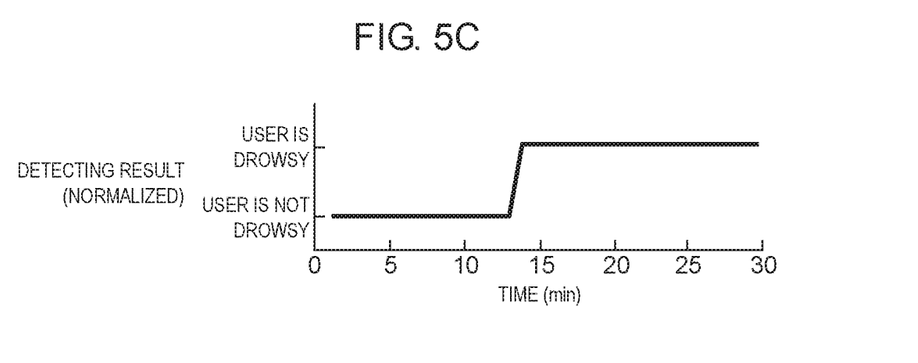
FIG. 5C is a graph showing an example of drowsiness detecting in a case where the feature value is normalized according to the first exemplary embodiment.

FIGS. 5A to 5C show examples of a drowsiness detecting result from continuous monotonous operation on a driving simulator for 30 minutes. In FIGS. 5A to 5C, a horizontal axis represents time, and a vertical axis represents "user is not drowsy" or "user is drowsy". FIG. 5A shows presence or absence of drowsiness based on a report made by a driver. FIG. 5B shows a detection result from a conventional method in which the feature value is not normalized. In other words, in FIG. 5B, drowsiness is detected from the feature value that has not been altered after being extracted by feature extractor 12. FIG. 5C shows a detection result from the method of the first exemplary embodiment in which the feature value is normalized. In other words, in FIG. 5C, drowsiness is detected from the feature value normalized based on feature values determined that "user is not drowsy".

In FIG. 5A, the driver reports "user is drowsy" 14 minutes after the start of the operation. In contrast, in the detection result from the conventional method shown in FIG. 5B, drowsiness is not detected and "user is drowsy" is detected 26 minutes after the start of the operation. On the other hand, in the detection result of the first exemplary embodiment shown in FIG. 5C, drowsiness detecting based on a difference from "user is not drowsy" is achieved. Accordingly, drowsiness detecting device 10 can detect "user is drowsy" at a timing 14 minutes after the start of the operation that is the same timing as the driver makes the report.

3. Effects and Other Benefits

As described above, drowsiness detecting device 10 according to the present exemplary embodiment includes feature extractor 12, detecting rule storage unit 14, feature normalizer 13, and drowsiness detector 15. Feature extractor 12 extracts the feature value on heartbeats of a user based on intervals between the heartbeats. Detecting rule storage unit 14 retains the detecting rule for drowsiness detecting. Feature normalizer 13 updates the normalization coefficient. Drowsiness detector 15 detects drowsiness of the user based on the feature value, the detecting rule, and the normalization coefficient. Feature normalizer 13 updates the normalization coefficient based on the feature value when drowsiness detector 15 does not detect the drowsiness of the user. Accordingly, accurate drowsiness detecting less susceptible to differences between individuals is achieved.

Drowsiness detecting device 10 further includes degree of confidence determination unit 16 that determines a degree of confidence of the drowsiness detected by drowsiness detector 15. In a case where the degree of confidence with which drowsiness detector 15 determines that the user is not drowsy is greater than the predetermined degree of confidence threshold value, feature normalizer 13 updates the normalization coefficient. Accordingly, the drowsiness can be accurately detected even for the same person and with time variations.

Drowsiness detecting device 10 further includes RRI detector 11 that receives the electrocardiogram wave and detects the RRI on the electrocardiogram wave. Feature extractor 12 extracts the feature value on heartbeats based on the RRI. Accordingly, the direct input of the electrocardiogram wave allows the drowsiness to be determined in real time.

Further, feature extractor 12 extracts the plurality of feature values F1 to F7. The plurality of feature values F1 to F7 are associated with the plurality of respective nodes N1 to N7 in the decision tree. With this configuration, the drowsiness can be detected and the degree of confidence of the drowsiness can be determined from the plurality of feature values. Accordingly, drowsiness detecting device 10 can more accurately perform the drowsiness detecting.

Further, feature normalizer 13 of the present exemplary embodiment calculates the normalization coefficient based on a feature value in which a degree of confidence determined by degree of confidence determination unit 16 in a range from the predetermined time before to a time immediately before the present time is greater than the predetermined degree of confidence threshold value. Accordingly, the drowsiness detecting can be effectively performed.

Further, feature normalizer 13 of the present exemplary embodiment calculates the normalization coefficient from the weighted sum of the previous normalization coefficient and the feature value in which a degree of confidence determined by degree of confidence determination unit 16 is greater than the predetermined degree of confidence threshold value. Accordingly, the drowsiness detecting can be effectively performed.

It should be noted that drowsiness detecting device 10 of the present exemplary embodiment includes RRI detector 11 that receives the electrocardiogram wave and detects the RRI. However, drowsiness detecting device 10 may include, in place of RRI detector 11, an RRI input unit that receives data on the RRI detected in a different way by an external device.

It should be noted that feature normalizer 13 of the present exemplary embodiment updates the normalization coefficient in a case where drowsiness detector 15 determines that "user is not drowsy" and a degree of confidence detected by degree of confidence determination unit 16 is greater than the predetermined degree of confidence threshold value. However, drowsiness detecting device 10 need not include degree of confidence determination unit 16. Accordingly, feature normalizer 13 may update the normalization coefficient in a case where drowsiness detector 15 determines that "user is not drowsy". In this case, the configuration of drowsiness detecting device 10 can be simplified.

It should be noted that, in the present exemplary embodiment, the decision tree and the random forest are exemplified as methods for drowsiness detector 15 to detect the drowsiness. However, the present disclosure is not limited to the methods. The method for detecting the drowsiness may be any method for detecting the drowsiness from a feature value on heart rate variability. For example, the drowsiness may be detected by a probability model based on the feature value on heart rate variability. This configuration allows degree of confidence determination unit 16 to use, as a degree of confidence to be determined, a probability value output from the probability model in a case where "user is not drowsy" is detected.

4-1. First Modified Example

Drowsiness detecting device 10 of the first exemplary embodiment described above receives the electrocardiogram wave as input and detects the RRI from the electrocardiogram wave thus input to detect the drowsiness. However, drowsiness detecting device 10 may receive, as input, a pulse wave in place of the electrocardiogram wave. This configuration allows the drowsiness detecting to be performed based on not only the electrocardiogram wave, but also the pulse wave measured at an earlobe or a wrist.

4-2. Second Modified Example

Figure 6:
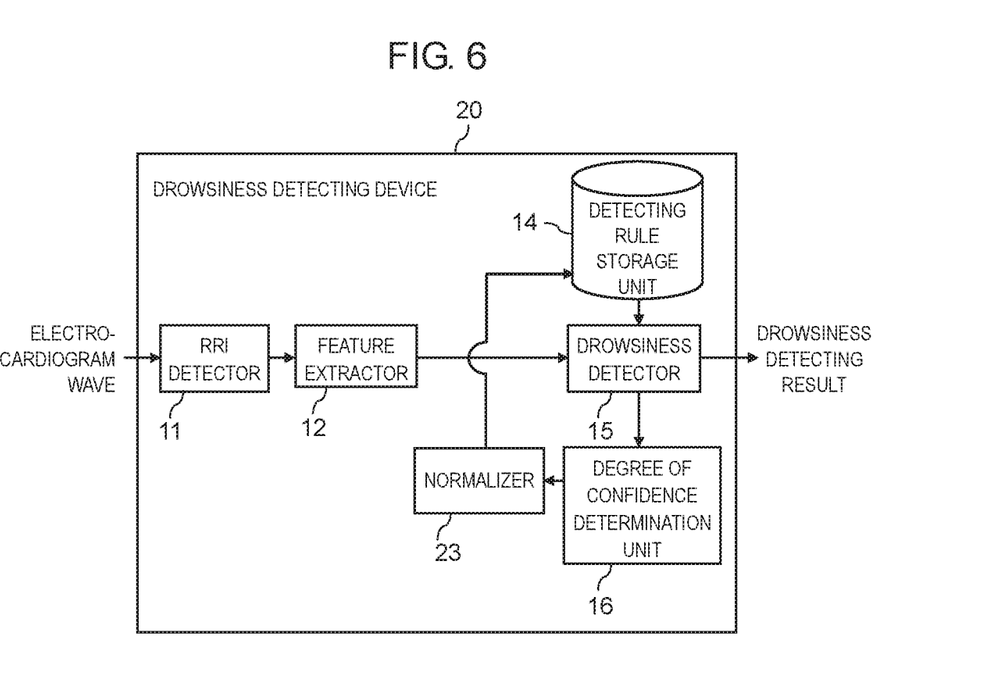
FIG. 6 is a block diagram of a drowsiness detecting device according to a second modified example.

A drowsiness detecting device according to a second modified example will be described with reference to FIG. 6. FIG. 6 is a block diagram of drowsiness detecting device 20 according to the present modified example.

Drowsiness detecting device 20 includes normalizer 23 in place of feature normalizer 13 of drowsiness detecting device 10 (refer to FIG. 1).

As with feature normalizer 13, normalizer 23 updates normalization coefficient $C_k$ based on the feature value from which drowsiness detector 15 does not detect the drowsiness of the user. Then, normalizer 23 normalizes, with normalization coefficient $C_k$, a rule threshold value of the detecting rule retained by detecting rule storage unit 14. Here, normalizer 23 may multiply each rule threshold value by normalization coefficient $C_k$ to normalize the rule threshold value. In drowsiness detecting device 10 illustrated in FIG. 1, the feature value thus normalized and the rule threshold value (threshold values T1 to T7) are compared in the decision tree. However, in drowsiness detecting device 20, the feature value that is not normalized and the rule threshold value thus normalized are compared. Then, drowsiness detecting device 20 detects the drowsiness of the user based on the feature value and the detecting rule including the rule threshold value thus normalized. As with drowsiness detecting device 10, this configuration allows the drowsiness detecting to be accurately performed.

Further, normalizer 23 may normalize both the feature value and the rule threshold value of the detecting rule with the normalization coefficient. Then, drowsiness detecting device 20 may detect the drowsiness of the user based on the feature value thus normalized and the detecting rule including the rule threshold value thus normalized.

The drowsiness detecting device and the like according to one or a plurality of aspects of the present disclosure have been described with reference to the exemplary embodiment. It should be noted, however, that the present disclosure is not limited to the above-described exemplary embodiment. Without departing from the scope of the present disclosure, various modifications conceived by those skilled in the art and applied to the present exemplary embodiment, and another embodiment constructed by a combination of constituent components in a different exemplary embodiment may be included in the range of one or a plurality of aspects of the present disclosure.

As described above, the exemplary embodiment has been described as an illustration of the technique in the present disclosure. For the description, the attached drawings and detailed description have been provided.

Therefore, the constituent components illustrated in the attached drawings and described in the detailed description may include, for the illustration of the above-described technique, not only constituent components essential for the solution to the problem, but also constituent components not essential for the solution to the problem. Thus, it should not be deemed that, merely based on the fact that the constituent components that are not essential have been illustrated in the attached drawings and described in the detailed description, the constituent components that are not essential are essential.

Further, since the aforementioned exemplary embodiment illustrates the technique of the present disclosure, various changes, replacements, additions, omissions, and the like can be made in the claims and their equivalents.

The present disclosure is applicable to a drowsiness detecting device or the like that performs accurate drowsiness detecting.

What is claimed is:

1. A drowsiness detecting device comprising:
   a feature extractor configured to extract a feature on heartbeats of a user based on intervals between the heartbeats;
   a detecting rule storage unit configured to retain a detecting rule for drowsiness detecting;
   a normalizer configured to update a normalization coefficient;
   a drowsiness detector configured to detect drowsiness of the user based on the feature, the detecting rule, and the normalization coefficient; and
   a degree-of-confidence determination unit configured to determine a degree of confidence of the drowsiness of the user detected by the drowsiness detector,
   wherein the normalizer updates the normalization coefficient based on the feature when the drowsiness detector does not detect the drowsiness of the user, and
   wherein, when the degree of confidence is greater than a predetermined degree-of-confidence threshold, the normalizer is further configured to update the normalization coefficient.

2. The drowsiness detecting device according to claim 1, wherein
   the normalizer normalizes the feature with the normalization coefficient, and
   the drowsiness detector detects the drowsiness of the user based on the detecting rule and the normalized feature.

3. The drowsiness detecting device according to claim 1, wherein
   the normalizer normalizes a rule threshold of the detecting rule with the normalization coefficient, and
   the drowsiness detector detects the drowsiness of the user based on the feature and the detecting rule including the normalized rule threshold.

4. The drowsiness detecting device according to claim 1, further comprising an R-R interval detector configured to receive an electrocardiogram wave and detect an R-R interval on the electrocardiogram wave,
   wherein the feature extractor extracts the feature on the heartbeats based on the R-R interval.

5. The drowsiness detecting device according to claim 1, further comprising an R-R interval input unit configured to receive an R-R interval on an electrocardiogram wave,
   wherein the feature extractor extracts the feature on the heartbeats based on the R-R interval.

6. The drowsiness detecting device according to claim 1, wherein
   the detecting rule is a rule based on a decision tree, and
   the degree-of-confidence determination unit determines the degree of confidence of the drowsiness of the user from a proportion of drowsiness in a leaf node of the decision tree.

7. The drowsiness detecting device according to claim 6, wherein
   the feature extractor extracts a plurality of the features, and
   the plurality of features are associated with a plurality of respective nodes of the decision tree.

8. The drowsiness detecting device according to claim 1, wherein
   the detecting rule is a rule based on a random forest including a plurality of decision trees, and
   the degree-of-confidence determination unit determines the degree of confidence of the drowsiness of the user from a proportion of drowsiness in the plurality of decision trees.

9. The drowsiness detecting device according to claim 1, wherein the normalizer updates the normalization coefficient based on the feature from which the drowsiness detector does not detect the drowsiness of the user, the feature being extracted in a range from a predetermined time before to a time immediately before a present time.

10. The drowsiness detecting device according to claim 9, wherein the normalizer updates the normalization coefficient based on a weighted sum of a previous normalization coefficient and the feature.

11. The drowsiness detecting device according to claim 10, wherein the greater the degree of confidence is, the greater a weight used for calculation of the weighted sum is.

12. A drowsiness detecting method comprising:
    extracting a feature on heartbeats of a user based on intervals between the heartbeats;
    updating a normalization coefficient;
    detecting drowsiness of the user based on the feature, the normalization coefficient, and a detecting rule for drowsiness detecting;
    determining a degree of confidence of the detected drowsiness of the user; and
    updating the normalization coefficient when the degree of confidence is greater than a predetermined degree-of-confidence threshold,
       wherein the normalization coefficient is updated based on the feature when the drowsiness of the user is not detected.

13. A non-transitory program recording medium recording a program that causes a computer to perform the drowsiness detecting method according to claim 12.

* * * * *